(12) United States Patent
Ruddle et al.

(10) Patent No.: US 8,235,719 B2
(45) Date of Patent: *Aug. 7, 2012

(54) APPARATUS FOR CLEANING A ROOT CANAL SYSTEM

(75) Inventors: Clifford J. Ruddle, Santa Barbara, CA (US); Robert H. Sharp, Sacramento, CA (US)

(73) Assignee: Endo Inventions, LLC, Santa Barbara, CA (US)

( * ) Notice: Subject to any disclaimer, the term of this patent is extended or adjusted under 35 U.S.C. 154(b) by 1518 days.

This patent is subject to a terminal disclaimer.

(21) Appl. No.: 11/227,934

(22) Filed: Sep. 15, 2005

(65) Prior Publication Data

US 2006/0234183 A1  Oct. 19, 2006

Related U.S. Application Data

(63) Continuation-in-part of application No. 11/104,678, filed on Apr. 13, 2005, now abandoned.

(51) Int. Cl.
*A61C 5/02* (2006.01)
(52) U.S. Cl. .......................................... 433/81
(58) Field of Classification Search .................. 433/102, 433/224, 81, 166; 604/272
See application file for complete search history.

(56) References Cited

U.S. PATENT DOCUMENTS

| 4,832,061 A |   | 5/1989 | Hwang |
| 5,725,370 A | * | 3/1998 | Himeno et al. ................. 433/86 |
| 5,775,346 A |   | 7/1998 | Szyszkowski |
| 5,775,902 A | * | 7/1998 | Matsutani et al. ............ 433/102 |
| 5,868,570 A |   | 2/1999 | Hickok et al. |
| 5,899,693 A |   | 5/1999 | Himeno et al. |

(Continued)

OTHER PUBLICATIONS

R. Gutaris et al., *In Vivo Debridement Efficacy of Ultrasonic Irrigation Following Hand-Rotary Instrumentation in Human Mandibular Molars*, JOE vol. 31, No. 3 pp. 166-170, Mar. 2005.

(Continued)

*Primary Examiner* — Heidi M Eide
(74) *Attorney, Agent, or Firm* — Polster, Lieder, Woodruff & Lucchesi, L.C.

(57) ABSTRACT

An endodontic tool is provided to facilitate the removal of the smear layer and to enhance deep lateral cleaning of a root canal system. The tool includes a sonic driven activator which is made from a strong, flexible, non-metallic, and non-cutting material. The activator can be smooth. A snap-on coupler is adapted to attach the tool to a driver via a snap on action and without the use of tools. The driver will vibrate, sonically or ultrasonically, the flexible activator within a root canal of a tooth. The tool can be provided with fluid passages which allow for irrigating reagents to be delivered through the activator and into the root canal space during endodontic procedures.

24 Claims, 3 Drawing Sheets

U.S. PATENT DOCUMENTS

| | | | |
|---|---|---|---|
| 5,952,605 A * | 9/1999 | Sievers et al. | 136/205 |
| 6,059,570 A | 5/2000 | Dragan et al. | |
| 6,085,761 A | 7/2000 | Inaba | |
| 6,162,202 A | 12/2000 | Sicurelli et al. | |
| 6,179,617 B1 * | 1/2001 | Ruddle | 433/224 |
| D441,141 S | 4/2001 | Shalita | |
| 6,290,503 B1 * | 9/2001 | Lemon et al. | 433/226 |
| 6,343,929 B1 | 2/2002 | Fischer | |
| 6,634,051 B1 | 10/2003 | Dragan et al. | |
| 6,638,067 B2 * | 10/2003 | Fischer et al. | 433/102 |
| 2002/0172922 A1 | 11/2002 | Manschedel | |
| 2003/0130626 A1 * | 7/2003 | VanTassel et al. | 604/272 |
| 2003/0152886 A1 * | 8/2003 | Houdt | 433/118 |
| 2003/0207231 A1 * | 11/2003 | Nance | 433/81 |
| 2004/0126732 A1 | 7/2004 | Nusstein | |
| 2004/0126738 A1 * | 7/2004 | Atkin et al. | 433/119 |
| 2004/0214135 A1 | 10/2004 | Ruddle | |
| 2005/0008673 A1 * | 1/2005 | Snyder et al. | 424/423 |
| 2005/0136375 A1 * | 6/2005 | Sicurelli et al. | 433/81 |

OTHER PUBLICATIONS

Sicurelli et al., Unpublished U.S. Appl. No. 10/741,175, filed Dec. 20, 2003 and entitled "Method and Apparatus to Remove Macro and Micro Debris From a Root Canal".

Cohen and Burns, Pathways of the Pulp, (2002) pp. 261-262.

Protest under 37 C.F.R. §1.291(a) submitted by Applicant C. Ruddle in U.S. Appl. No. 10/741,175, Sep. 23, 2005.

Declaration of Applicant C. Ruddle submitted with Protest in U.S. Appl. No. 10/741,175, Sep. 23, 2005.

* cited by examiner

APPARATUS FOR CLEANING A ROOT CANAL SYSTEM

CROSS-REFERENCE TO RELATED APPLICATIONS

This application is a continuation-in-part of application Ser. No. 11/104,678 filed Apr. 13, 2005 now abandoned entitled "Apparatus For Cleaning A Root Canal System" and which is incorporated herein by reference.

STATEMENT REGARDING FEDERALLY SPONSORED RESEARCH OR DEVELOPMENT

Not Applicable.

BACKGROUND OF THE INVENTION

This invention relates to endodontic tools, and in particular, to tools used during and after an endodontic root canal preparation procedure, to more effectively clean the root canal system prior to obturation.

Following tooth maturation, the dental pulp is harbored within the structural elements of the tooth. Frequently, and for a variety of reasons, the pulp is irreversibly injured, resulting in inflammatory and infectious conditions which often adversely affect the tooth, its supporting structures, and the patient's health. Clinically, as an alternative to extraction, root canal treatment is performed and ideally directed towards the elimination of pulp, bacteria, and related irritants from the root canal system, followed by three-dimensionally filling the root canal space with an inert, biocompatible, dimensionally stable, filling material, such as gutta percha. Ideally, the obturation procedures will fill not just the main canal, but the fins, webs, cul-de-sacs, lateral canals, and all portals of exit between the root canal system and the tooth's attachment apparatus.

Root canal procedures are common. Central to a successful endodontic treatment has been the use of chemical reagents during mechanical root canal shaping procedures to completely clean all aspects of the root canal system. The chemicals used to enhance canal debridement and disinfection during cleaning and shaping procedures potentially reach all aspects of the root canal system. The most popular chemicals currently used during canal preparation to actively assist in cleaning and disinfecting include bleach, hydrogen peroxide, and chelating agents. Often, a 2%-5% solution of a clear, pale, greenish-yellow strongly alkaline solution of sodium hypochlorite (NaOCl) and ethylenediaminetetracetic acid (EDTA) are used.

During canal preparation, a solution of NaOCl is liberally irrigated into the root canal space where its solvent action facilitates the digestion and removal of pulp, bacteria, viruses, spores, endotoxins and other irritants generated by the microorganisms. This solution has the potential to circulate, penetrate and, hence, clean into all aspects of the root canal space. However, studies have shown that even the most thorough use of sodium hypochlorite does not remove all the material from the root canal. The walls of a root canal are comprised of dentin, which contains millions of dentinal tubules per square millimeter. Instruments used to negotiate and shape a canal cut dentin and dentin, in combination with organic substrates, forms dentinal mud. Dentine mud, pulp, bacteria, and other related irritants have been consistently visualized histologically after cleaning and shaping procedures in the dentinal tubules and various aspects of the root canal systems. Thus, after cleaning and shaping procedures, the root canal is still covered with a film of debris, frequently described in the literature as a "smear layer." This "smear layer" includes dentinal mud and/or organic debris, including the irritants noted above.

After cleaning and shaping, the root canal has been traditionally filled with gutta percha and a root sealer. However, if the smear layer or film is not adequately removed from the root canal, the smear layer can compromise the filling and sealing of the root canal system. If obturation is incomplete then the root canal space is predisposed to bacterial leakage and failure. Post-treatment failures attributable to leakage are common and require endodontic retreatment of the tooth or extraction. Thus, for a complete and thorough cleaning, this smear layer or film should be removed. To address the smear layer, practitioners use a weak acid or surfactant, such as 17% EDTA, in an effort to remove the smear layer. Typically, the root canal is flushed with EDTA, or other similar reagents, to accomplish this. Traditionally, some practitioners have used a metal root canal file or a cannula to activate the solution and enhance the performance of the EDTA. These devices may be used manually or mounted in an ultrasonic handpiece to produce vibrations and fluid movement. As an example, even when a file is used, it is impossible to ensure that the file is brought into contact with the complete surface of the root canal, and hence it is difficult to ensure that substantially all of the smear layer has been removed. Regrettably, the use of ultrasonically driven metal instruments has frequently led to iatrogenic events, such as broken instruments, ledges in the wall of the root canal preparation, or even perforation of the root canal.

In my prior patent, U.S. Pat. No. 6,179,617, which is incorporated herein by reference, I disclosed an endodontic brush for use in removing the smear layer. The brush is comprised of a handle, a shank and a brush section extending from the shank. The brush section includes a plurality of bristles extending from a twisted wire core. While this brush works acceptably, it still has many shortcomings which are due to the fact that the core and shank are disclosed to be made from wire. The two twisted wires which form the core and shank are each 0.2 mm in diameter, and hence, the core and shank have a diameter of at least 0.4 mm. While the wires are quite thin, even without bristles, the device, at times, has a diameter that is too large to reach the end of many canals. From a technical standpoint, the wires cannot be made much thinner because the brush would then become predisposed to breakage during use. Even at the current diameter, the wire shank and core are too flexible. Because of its high flexibility, an endodontist cannot effectively and purposely brush the sides of the root canal wall, using a brushing manner, and hence cannot thoroughly remove the smear layer from the root canal preparation. Additionally, because of the twisted wire core, the brush cannot be driven ultrasonically. The twisted wire core prevents the optimal transfer of ultrasonic energy to the bristles of the brush.

Since the brush is too large for well-prepared, yet smaller diameter canals, I have found that when the brush is placed into the canal, the irrigant in the canal is partially displaced by the brush. This is undesirable as it is the irrigant that dissolves the smear layer. Whether the brush, disclosed in my above noted patent, or a file, is used to clean a prepared canal, the addition of fresh irrigant requires that either tool be removed from the canal to allow for fresh irrigant to be introduced into the canal.

Additionally, prior sonic or ultrasonically driven endodontic tools require that the tool be attached to a driver by means of wrenches. This makes it difficult (and sometimes time consuming) to change tools during a procedure. It would be desirable to make it easier to attach the tools to, and remove then from, their drivers.

BRIEF SUMMARY OF THE INVENTION

Briefly stated, an endodontic tool or activator is provided to facilitate the removal of the smear layer and organic debris from the root canal system after an access cavity to the root canal has been formed, the root canal orifices have been exposed, and the canals shaped to substantially remove organic materials from the root canal. The tool comprises a cup-shaped guard, a snap-on coupler, and an activator extending from the coupler. The activator includes a connecting portion and a flexible, activating portion. The coupler is adapted to snap on to a sonic driver or thread onto an ultrasonic driver to be connected thereto. By enabling the tool to be snapped onto a driver, the tool can be connected to its driver without the use of tools (such as wrenches), as is required by the threaded connection. The tool can also be adapted to be connected to the driver by other means, such as a latch-type connection, a frictional connection, a chuck grip connection, etc.

The activator is made from a flexible, non-metallic, non-cutting material. The activator can, for example, be made from plastic, nylon, or an aromatic polyamide (such as Kevlar®). The activator can be generally straight (for connection to a contra-angled handpiece) or it can be contra-angled (for connection to a straight handpiece). The activating portion can be substantially parallel (i.e., generally cylindrical) or tapered in design. The activating portion surface can be smooth. The activating portion is narrow at its apical or distal end and can have diameters as small as about 0.1 mm to about 0.2 mm at its apical or distal end. At its largest diameter, the apical end of the activating portion can have a diameter of about 1 mm. Of critical importance, this size allows for the tip of the activating portion to reach to the end of a prepared root canal. The activating portion, if tapered, has a taper of between about 0.01 mm/mm and about 0.12 mm/mm.

In one variation of the activator, a lumen extends through at least a part of the overall length of the activator. The activator can be provided with one or more pores along its lateral surfaces extending from the lumen to the external surface of the device. Preferably, the pores are formed in the activating portion only of the activator. If there are a plurality of pores, then the pores can have a diameter substantially smaller than the diameter of the lumen. Thus, for example, the pores can have a diameter of about 0.001 mm to about 0.2 mm and the lumen can have a diameter of about 0.1 mm to about 0.5 mm, depending on the overall size of the tool. The lumen extends through the activator, the entrance to the lumen being at the more proximal end of the tool. In one variation, the pores do not extend to the very distal end of the activating portion. Thus, for example, the activating portion could be free of pores between, for example, $D_0$ and $D_1$. In another variation, the activating portion can be provided with pores which extend over the full length of the activation portion. In this variation, the pores at the distal end of the activating portion (i.e., the pores from $D_0$ to, for example, $D_1$) can have a diameter smaller than the remaining pores in the activating portion.

In use, the method of cleaning a root canal system using the tool of the present invention comprises (1) preparing an access cavity in the patient's tooth; (2) exposing the orifice(s) of the root canal system within the pulp chamber of the tooth; (3) mechanically preparing the canal to facilitate chemically flushing and removing organic substrates from the root canal; (4) repeatedly irrigating and flushing the expanding preparation during shaping procedures to remove the smear layer from the internal walls of the shaped canal; (5) repeatedly irrigating and flushing to encourage the circulation and deep lateral penetration of the chemical reagent into all aspects of the root canal system; (6) agitating the chemical reagents in the root canal system with a sonically or ultrasonically driven activator, which has a strong, highly flexible and tapered design made from a non-metallic, non-cutting material. When the activator is provided with an internal lumen and lateral pores, the method additionally includes passing fresh intracanal irrigating reagents through the lumen and side pores while agitating the tip within the root canal.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figures 1, 1A:
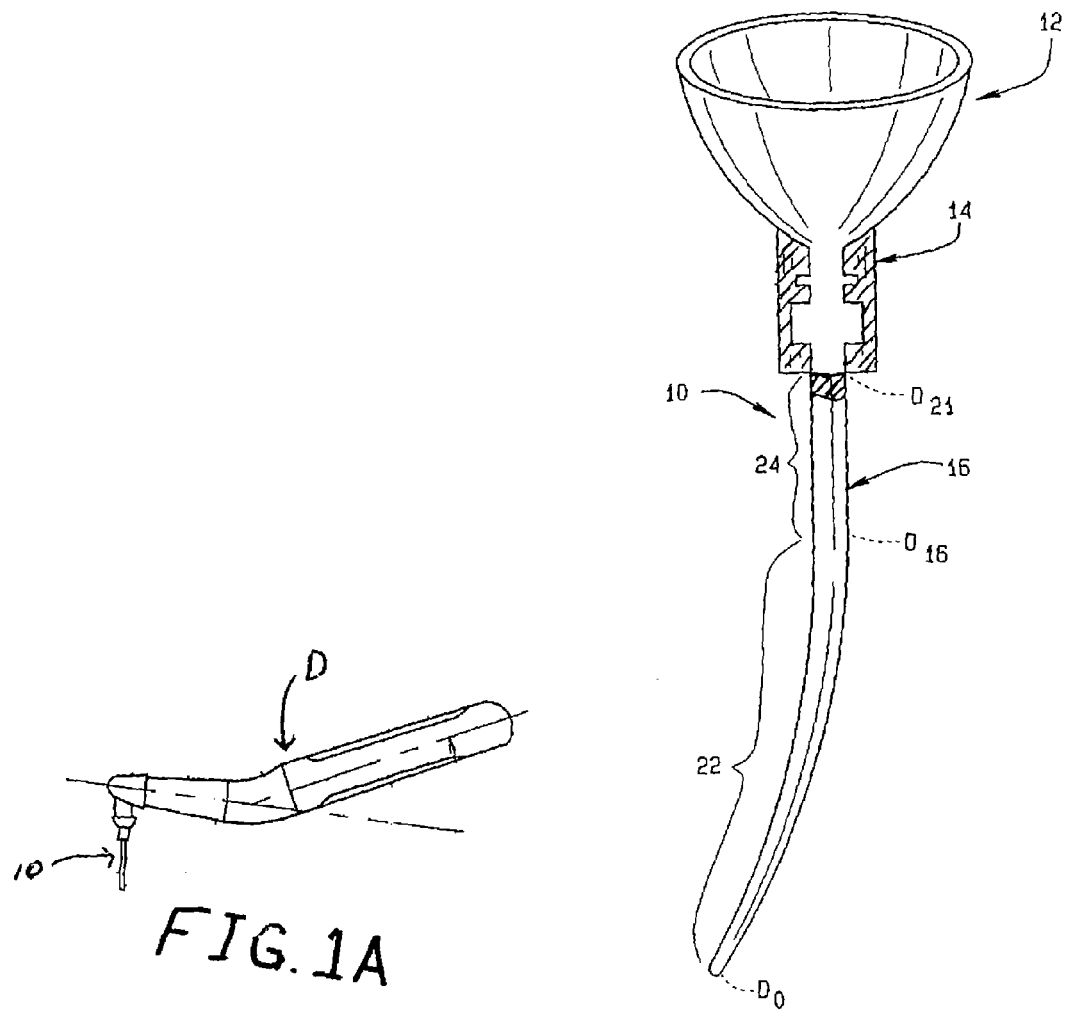
FIG. 1 is an elevational view of an illustrative embodiment of an endodontic tool of the present invention with a coupler portion of the tool being shown in cross-section.
FIG. 1A is a side elevational view of the endodontic tool mounted to a sonic driver.

The following detailed description illustrates the invention by way of example and not by way of limitation. This description will clearly enable one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

An illustrative endodontic tool 10 made in accordance with one aspect of the present invention includes a hollow guard 12 at the proximal end thereof, a snap-on coupler 14 below the guard 12 and an activator 16 extending from the coupler 14. As will be described more fully below, the activator 16 is sized to be received in the root canal of a tooth during and after a root canal preparation procedure, and to extend to the full length of the root canal.

Figure 2:
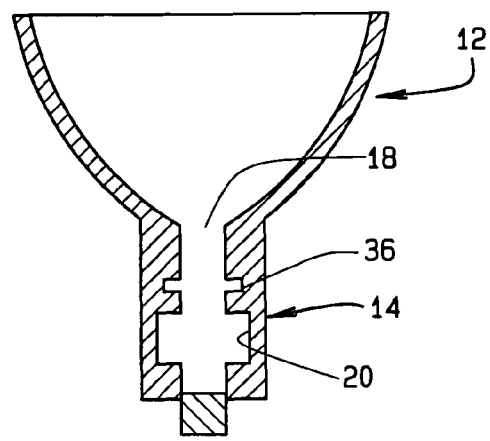
FIG. 2 is a cross-sectional view of an proximal end of the device, showing the guard and the connector which enables the device to be connected to a driver.

As seen in FIG. 2, the hollow guard 12 is essentially cup-shaped and has an opening 18 at the bottom thereof. The opening 18 leads into the connector 14. The guard 12 and coupler 14 are sized and shaped to receive the end of a sonic driver D which will vibrationally drive the activator 16. The driver can, for example, be a driver as shown and described in our U.S. Pat. No. 7,261,561, entitled "Vibrational Driver For Endodontic Activators" and which is incorporated herein by reference. The cup-shaped guard forms a shield about the driver during use to reduce the amount of fluids or aerosols that will spray against the driver during use.

The coupler 14 is adapted to removably engage the end of the driver. As shown in FIGS. 1 and 2, the coupler 14 includes a recess 20 which can receive a projection on the tip of the driver. The recess 20 can comprise one or more discrete holes, depressions, notches, etc. spaced about the inner circumference of the coupler (as shown in the figures) or a continuous circumferential groove. Alternatively, the recess 20 could be replaced with a rib or series of discrete projections or even spring mounted pins or balls, which would then be received in a groove or series of notches/indentations in the driver tip.

The activator 16 comprises two portions, an activating portion 22 and a connecting portion 24. The activating portion 22 has a length of about 16 mm, and has a diameter $D_0$ at the distal tip thereof and a diameter $D_{16}$ at the upper end of the activating portion 22. The activating portion 22 can have generally straight sides but is preferably tapered. The activating portion can be cylindrical, square, rectangular, triangular, or paddle shaped; and each of these shapes can then be either generally straight or tapered. The activating portion 22 has a distal tip diameter $D_0$ of between about 0.1 mm or 0.2 mm and up to about 1.5 mm, and a proximal diameter $D_{16}$ of between about 1 mm and 2 mm at its most proximal end. The taper of the activating portion can be between about 0.01 mm/mm and about 0.12 mm/mm (i.e., between about 1% and about 12%).

The connecting portion 24 has a length of between about 2 mm and about 15 mm, such that the overall length of the activator 16 is between about 18 mm and about 31 mm. The activator connecting portion 24 can be generally cylindrical. Alternatively, the connecting portion 24 can continue the taper of the activating portion 22.

The tool 10 can be made available in multiple sizes, such as small, medium, and large, to cover variations in the diameter of fully shaped canals following root canal preparation procedures. Additionally, the overall length of the activators can vary to address the variations in the working lengths of teeth. For example, the activators can be about 18, 21, and up to 31 mm in overall length. Thus, for example, the small tool can have a $D_0$ tip diameter of about 0.1 or 0.2 mm and a $D_{16}$ diameter of about 0.52 mm; the medium tool can have a $D_0$ tip diameter of about 0.3 mm and a $D_{16}$ diameter of about 0.94 mm; the large tool can have a $D_0$ tip diameter of about 0.5 mm and a $D_{16}$ diameter of about 1.5 mm. These are examples of three possible dimension combinations. Of course, the diameters of the activating portion 22 can vary to accommodate different sized root canals. Thus, the $D_0$ diameter can be as large as 1.5 mm and the $D_{16}$ diameter can be as larger as 2 mm. The connecting portion of the activator from $D_{16}$ to the bottom of the coupler 14 as noted above, can either continue to taper or be generally cylindrical. The activator 16 can be permanently fixed to the snap-on coupler 14, which in turn is attached to the guard 12. The three tools each have different diameters and tapers and are provided as a set. Each tool comprises a proximal guard 12, a snap-on coupler 14, and a distal activator 16. The tool 10 can then be used as needed, as will be described further below.

The activator 16 is formed from a strong, highly flexible, smooth, non-metallic and non-cutting material. The activator 16 is shown in FIG. 1 in a bent or curved position. This is to show some of the flexibility of the activator 16. In fact, the activator 16 is sufficiently flexible to be bent into a U-shape. The tool 10 can be made from a variety of materials such as plastic, nylon, or an aromatic polyamide containing elastomers, such as are available from E. I. du Pont de Nemours and Company under the name Kevlar®. Nylon, for example, can be manufactured with different $D_0$ diameters and tapers to provide a strong, highly flexible activating portion 22 that can safely pass through canals that exhibit multiplanar curvatures.

The activating portion 22 has a smooth surface. However, if desired, the surface of the activating portion can be flocked and/or textured.

The tool 10, as noted above, is adapted at its proximal end to receive a male driver which extends through the guard 12 and into the coupler 14. The driver includes a sonic or ultrasonic generator. Such a driver can use piezoelectric or magnetostrictive elements, for example. In our work, we have found that a Water Pik® driver, commercially available from Water Pik, Inc. of Newport Beach, Calif., works well as a sonic driver for the activator 16. A preferred driver for sonic applications is the driver described in our above noted application Ser. No. 11/182,093 filed on Jul. 15, 2005, entitled "Vibrational Driver For Endodontic Activators" and which is incorporated herein by reference.

When the activating portion 22 is inserted into a fluid-filled and shaped root canal, and its driver activated, the sonic energy of the driver will, due to the shape of the activating portion 22, cause the flexible most distal tip of the activating portion 22 to vibrate in the fluid in the root canal, which is termed cavitation; vigorous movement of fluids lateral to the activating portion 22 is termed acoustic streaming. If the driver is a sonic driver, the activating portion 22 can vibrate between about 1 KHz to 10 KHz; if the driver is a magnetostrictive generator, the activating portion will vibrate at about 15-24 KHz; and if the driver is a piezoelectric ultrasonic generator, the activating portion 22 will vibrate at about 22 Khz to 40 KHz. Because the activating portion 22 is very strong and flexible, the vibrations induced in the activating portion 22 by the driver will cause cavitation and acoustic streaming of the solution within the root canal. This phenomenon will dislodge and remove the smear layer from the prepared walls of the canal and, further, serve to provide a technique for deep lateral cleaning into all aspects of the root canal system. To maximize cavitation and acoustic streaming, the canal must be filled with irrigating solutions, such as sodium hypochlorite, EDTA as discussed above, or other final rinse solutions. The activating portion 22 of the tool 10 is shaped such that when the tool is activated within a root canal filled with the irrigating solution, the vibrations of the more distal tip within the root canal will cause the irrigating solution to cavitate. Agitating the intracanal irrigant lateral to the activator will initiate acoustic streaming; together, cavitation and acoustic streaming cause the intracanal irrigating solution to become turbulent, facilitating the removal of the smear layer and promoting deep lateral cleaning within the root canal system.

Stated differently, by driving the flexible, non-cutting, and non-metallic activator 16, even at only sonic speeds, the turbulence induced to the irrigating solution by the vibrating activator will enhance the effectiveness of the irrigating solution by bringing more of the solution into contact with the walls of the root canal and into the inaccessible areas of the root canal system. Additionally, as the activator 16 vibrates within the root canal, its lateral walls will contact and rub against the surfaces of the root canal to physically enhance the chemical action of the irrigating solution. This action will result in a better removal of the smear layer within the root canal than can be accomplished with, for example, files. Further, because the activator is made from a non-metallic and non-cutting material, as noted above, the physical action of the tool within the root canal will not damage the internal walls of the canal. Specifically, the use of the activator 16 will not result in apical transportation or ledge formation within the canal, which can occur when using stiffer devices, such as metal files or cannuli. Further, this method of cleaning will reduce the possibility of other iatrogenic events.

In another embodiment, the tool (FIGS. 3-4) can be provided with an internal lumen or flow path 30, which extends through the activating portion 22' and at least a part of the connector portion (not shown in FIG. 3 or 4) of the tool. The lumen 30 does not extend to the most distal end or tip of the activating portion 22, but rather ends short of the distal end, as seen in FIG. 4. This lateral design feature safely confines the irrigant to the root canal. A plurality of small openings or pores 32 extend from the lateral surfaces 34 of the activating portion 22 to the lumen 30. The pores 32 are shown to extend generally radially, but could extend from the lumen 30 at some other desired angle. The pores are located only in the activating portion 22 of the activator 16', and thus are formed only between the diameters $D_0$ and $D_{16}$ of the activator 16'. The connecting portion 24 (which generally will not extend into a tooth) will be free of pores.

The size of the lumen 30 and the pores 32 is determined in part by the size of the activator 16. The lumen 30 can have a diameter of between about 0.1 mm and about 0.5 mm. The pores 32 have a diameter smaller than the diameter of the lumen 30. The pore diameter can be between 0.001 mm and about 0.2 mm.

Figure 3:
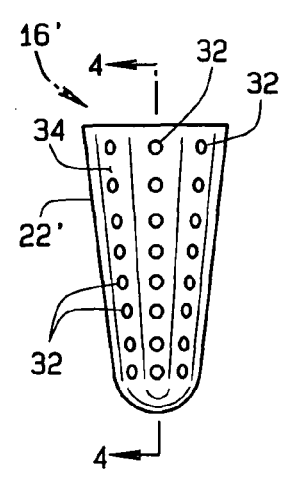
FIG. 3 is an enlarged fragmentary elevational view of a second illustrative embodiment of the endodontic tool.
Figure 4:
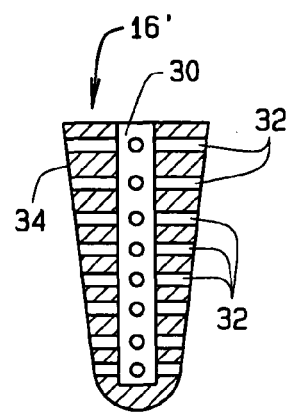
FIG. 4 is an enlarged cross-sectional view taken along line 4-4 of FIG. 3.

The pores 32, as seen in FIGS. 3 and 4, do not extend to the very distal end of the activating portion 22. Rather, they end short of the very distal end. For example, the pores can be absent from the region between $D_0$ and $D_1$.

Figure 5:
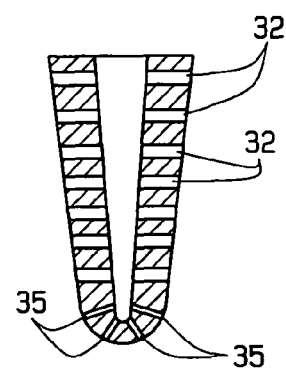
FIG. 5 is an enlarged cross-sectional view of a variation of the tool of FIGS. 3 and 4.

However, as seen in FIG. 5, pores 35 can be formed to extend from the end of the lumen 30 to the activator surface between $D_0$ and $D_1$ (i.e., the area which is void of pores 32). The pores 35 can be the same size as the pores 32, or can be smaller than the pores 32. For example, the pores 35 can be as small as 0.001 mm (1 micron).

The activator 16' is shown to have a plurality of pores which exit laterally from the side of the activator or near the bottom of the activator. The activator could, instead, be provided with a single pore which exits either along the side or lateral of surface 34 of the activator or proximate the apical end of the activator. If the pore exits from the side or lateral surface of the activator, the fluid flow path defined by the lumen 30 and the exit pore would generally be L-shaped. It will be appreciated that such an L-shaped flow path could define an angle of less than 90°, or otherwise have a curvature to facilitate the flow of fluid through the flow path and to reduce pressure losses in the fluid stream due to bends in the flow path. If the pore exits just proximal to the distal end of the activator, the fluid flow path can be generally straight or have a slight curvature near the bottom. Because there is only a single pore or exit opening, the exit can have a diameter that is generally equal to the diameter of the lumen 30. Alternatively, this single exit pore could have a diameter, as described above, which is smaller than the diameter of the lumen 30.

As noted above, the lumen 30 extends at least through a part of the activator connecting portion 24, to enable the activator 16 to be connected to a source of irrigant, and into the activating portion as described above. In one embodiment, the lumen 30 can extend through the activating portion 22 and the connecting portion 24 to open into the coupler 14. The snap-on coupler 14 of the tool, in turn, is constructed to be connected to a source of irrigant, which can be associated with the driver. To provide for a fluid tight seal between the coupler 14 and the driver, a groove 36 (FIG. 2) can be provided to receive an O-ring. Alternatively, the O-ring or other seal can be provided on the driver. The O-ring will form a liquid-tight seal between the tool connector and the liquid output from the drive. Thus, in addition to sonically vibrating the activator 16', the driver will also deliver irrigant through the lumen 30 and out through the pores 32 (and pores 36 if provided). In general, the irrigant will exit along the lateral sides of the activating portion 22', or depending on the construction of the activator, the irrigant may exit as a mist through the smaller pores 36 extending from the lumen 30 to the most distal aspect of the activating portion. Thus, during the irrigating procedure, as described above, the root canal will be supplied with fresh irrigant during the irrigating process to replace used irrigant. When energized by the driver, the activating portion 22 of the tool 10 produces cavitation and acoustic streaming, which are optimized in a canal filled with fresh irrigant.

Figure 6:
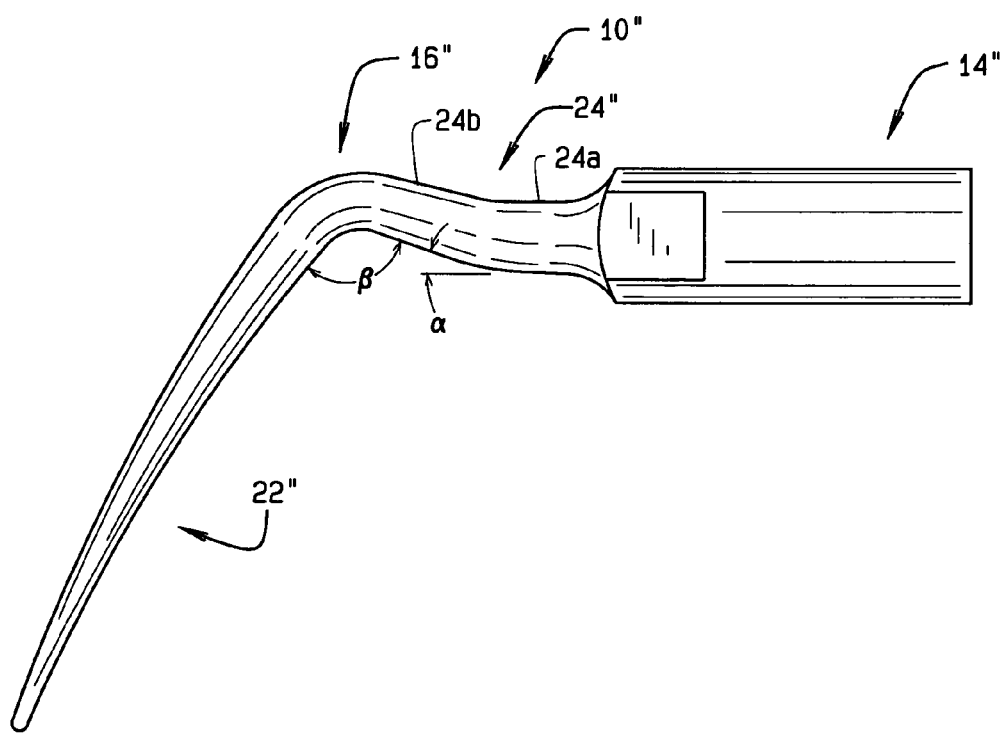
FIG. 6 is a side elevational view of the activator formed as a contra-angled tool.

A further embodiment of the activator is shown in FIG. 6. The activator 10", as can be seen, is a contra-angled activator. The activators 10 and 10' on the other hand are "straight" activators. The straight activators 10 and 10' are designed to be received on a contra-angled handpiece. The activator 10", on the other hand, is designed to be received on a straight ultrasonic handpiece, such as is commercially available from SybronEndo, Obtura Spartan, Tulsa Dental, etc. The structure and function of such handpieces are well known to those skilled in the art and will not be described or shown herein.

The activator 10" includes a coupler 14" which is configured, as known in the art, to enable the activator 10" to be mounted to a commercially available straight, ultrasonic handpiece, as just described. Thus, the coupler 14" will have a threaded bore which allows the activator 10" to be threaded onto an end of the handpiece. Additionally, the coupler includes at least some flat faces to enable the activator to be tightened down on the handpiece by the use of a wrench or other tool. An activator 16" extends from the coupler 14" and comprises a connecting portion 24" which extends from the coupler 14" and an activator portion 22" which extends from the connecting potion. The activator 16" is shaped, as seen in FIG. 6, to form a contra-angle. To this end, the connecting portion 24" includes a portion 24a and a second portion 24b. The first portion 24a is generally co-axial with, and extends generally straight from, the end of the coupler 14". The second portion 24b is angled upwardly relative to portion 24a, with respect to the drawing of FIG. 6. The angle between portions 24b and 24a can define an angle α of about 85°. The activator portion 22" then extends forwardly and downwardly from the end of the connecting portion 24b, and forms an angle β therewith of about 90°. The size of the angles defined by the activator 16" can vary, as is known to those skilled in the art. As with the tools 10 or 10', at least the activator 16" is made from a non-metal, non-cutting material, as described above in connection with the tool 10. The coupler 14Δ is preferably made from the same material as the activator 16", but can be made from a different material, if desired. The activator 16" can be solid, as is the activator 16, or can be provided with one or more pores, in the same manner as the activator 16'.

As various changes could be made in the above constructions without departing from the scope of the invention, it is intended that all matter contained in the above description or shown in the accompanying drawings shall be interpreted as illustrative and not in a limiting sense. Although the activator is shown and described to be adapted to be snapped or threaded onto a driver, the activator can be adapted to be connected or attached to the driver in other ways. For example, the activator can be adapted to be attached to the driver via a latch-type connection, a friction grip connection, a chuck-type connection, or any other type of connection which will enable the driver to induce vibrations in the activator portion of the activator tool. The activator portion (22, 22', 22") is shown to be circular in cross-section and tapered over its length. As noted above, the activator portion can be generally straight (rather than tapered) and can be provided with other cross-sectional shapes, as may be desired. These examples are merely illustrative.

The invention claimed is:

1. A tool for activating intracanal irrigants during endodontic procedures, the tool comprising:
   a coupler; said coupler being a snap-on coupler shaped and configured to receive or be received by a portion of a sonic driver to positively connect the tool directly to a vibrated member of the sonic driver,
   a flexible activator extending distally from the coupler; the activator being shaped such that when said sonic driver is activated, said sonic driver will induce vibrations in at least a portion of the activator; the activator comprising tapered activating portion having an elongate tapered side wall and being sized to extend through prepared root canals of teeth; said activating portion being shaped to induce cavitation and acoustic streaming in a fluid-filled root canal of a tooth when vibrations of a sonic frequency are induced in said activator to enhance deep lateral cleaning of the root canal system of the tooth; the activating portion being made from a flexible, non-cutting material,
   a flow path, said flow path comprising a lumen which extends through at least a part the activator and an exit opening on a surface of the activator; said exit opening being sized such that fluid exits the activator portion through the exit opening as a mist; the exit opening comprises a plurality of pores, said pores being formed only on the activating portion of the activator; the pores having a diameter substantially smaller than the diameter of the lumen; said flow path including pores at a distal end of the activating portion, wherein the pores at the distal end of the activating portion are smaller than pores above the distal end of the activating portion.

2. The tool of claim 1 wherein the pores at the distal end of the activating portion are between 0.001 mm and 0.01 mm in diameter.

3. A tool for use in endodontic procedures comprising:
   a coupler shaped and configured to snappingly connect the tool directly to a sonic vibratory driver, and
   a flexible activator extending from an end of the coupler and having a smooth outer surface; said activator having an elongate tapered side wall; said activator being sized to extend into a prepared root canal and shaped to induce cavitation and acoustic streaming in the fluid of a fluid-filled root canal of a tooth when vibrations are induced in said activator to enhance deep lateral cleaning of the root canal system of the tooth; the activator being made from a strong, flexible, non-metallic and non-cutting material; the activator including a flow path; said flow path comprising a lumen extending through at least a part of its length and an exit opening along a surface of the activator; said exit opening comprising a plurality of pores sized such that fluid exits the activator portion through the exit opening as a mist; the pores having a diameter of about 0.001 mm to about 0.2 mm and the lumen has a diameter of about 0.1 mm to about 0.5 mm; said pores comprising a plurality of first pores and a plurality of second pores; the first pores being positioned at a distal end of the activator and the second pores being positioned axially above the first pores along the activator to exit along a lateral surface of the activator; the first pores being smaller in diameter than the second pores.

4. The tool of claim 3 wherein said lumen communicates with the coupler.

5. A tool for use in endodontic procedures comprising:
   a coupler sized, shaped and configured to snappingly connect the tool directly to a sonic vibratory driver, said coupler including a groove to receive an O-ring to form a seal between said tool and said driver; and
   a flexible activator extending from an end of the coupler and having a smooth outer surface; said activator having an elongate tapered side wall; said activator being sized to extend into a prepared root canal and shaped to induce cavitation and acoustic streaming in the fluid of a fluid-filled root canal of a tooth when vibrations are induced in said activator to enhance deep lateral cleaning of the root canal system of the tooth; the activator being made from a strong, flexible, non-metallic and non-cutting material; the activator including a flow path; said flow path comprising a lumen extending through at least a part of its length and an exit opening along a surface of the activator; said exit opening being sized such that fluid exits the activator portion through the exit opening as a mist.

6. An apparatus for cleaning a prepared root canal during an endodontic procedure comprising:
   a sonic driver comprising a tip which is vibrated sonically when the driver is activated, and;
   a tool connected to the tip of the driver; the tool comprising:
   a coupler shaped and configured to mate to the tip of the sonic driver to positively and directly connect the tool to the tip of the sonic driver; and
   a flexible activator extending distally from the coupler; the activator being having an elongate tapered side wall to define a tapered activating portion; the taper of said activating portion being sized to extend into a prepared root canal of a tooth and being shaped to induce cavitation and acoustic streaming in fluid in the prepared root canal when sonic vibrations are induced in said activator to enhance deep lateral cleaning of the root canal system of the tooth; the activating portion being made from a flexible, non-cutting, non-metal, polymeric material.

7. The apparatus of claim 6 wherein the tool comprises a guard proximate the coupler; the guard being sized and shaped to cover a portion of the driver to which the tool is connected.

8. The apparatus of claim 6 wherein the activator is contra angled.

9. The apparatus of claim 6 wherein the activator includes a connecting portion extending between the coupler and the activating portion.

10. The apparatus of claim 6 wherein the tool further comprises a flow path, said flow path comprising a lumen which extends through at least a part the activator and an exit opening on a surface of the activator; said exit opening being sized such that fluid exits the activator portion through the exit opening as a mist.

11. The apparatus of claim 10 wherein the exit opening comprises a plurality of pores, said pores being formed only on the activating portion of the activator.

12. The apparatus of claim 11 wherein the activating portion is free of pores at a distal end of the activating portion.

13. The apparatus of claim 11 wherein the pores are of a diameter substantially smaller than the diameter of the lumen.

14. The apparatus of claim 13 wherein the pores have a diameter of about 0.001 mm to about 0.2 mm and the lumen has a diameter of about 0.10 mm to about 0.5 mm.

15. The apparatus of claim 14 wherein the activator comprises a plurality of first pores and a plurality of second pores; the first pores being positioned at the distal end of the activator and the second pores being positioned axially above the first pores along the activator to exit along a lateral surface of the activator.

16. The apparatus of claim 13 including pores at the distal end of the activating portion.

17. The apparatus of claim 6 wherein the activating portion has a $D_0$ diameter, at its most distal end, as small as about 0.1 to about 0.2 mm.

18. The apparatus of claim 6 wherein the taper of the activating portion ranges from between about 0.01 mm/mm and about 0.12 mm/mm.

19. The apparatus of claim 6 wherein the coupler is a snap-on coupler adapted to receive, or be received by, a portion of said driver.

20. The apparatus of claim 6 wherein the activating portion is made from a non-metallic material.

21. The apparatus of claim 20 wherein the activator is made from plastic, nylon, aromatic polyamide, or other suitable non-metallic material.

22. The apparatus of claim 6 wherein the activating portion is tapered along at least a part of its length.

23. The apparatus of claim 6 wherein the activating portion has a smooth axial outer surface and a distal end.

24. The apparatus of claim 6 wherein the material from which the activator is made is chosen from the group consisting of plastics, nylons, and aromatic polyamides.

* * * * *